(12) United States Patent
Moszner et al.

(10) Patent No.: US 8,921,450 B2
(45) Date of Patent: Dec. 30, 2014

(54) DENTAL MATERIALS BASED ON DIMER ACID DERIVATIVES WITH RING OPENING POLYMERIZABLE GROUPS

(75) Inventors: Norbert Moszner, Mauren (LI); Jörg Angermann, Sargans (CH); Urs Karl Fischer, Arbon (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 831 days.

(21) Appl. No.: 13/175,988

(22) Filed: Jul. 5, 2011

(65) Prior Publication Data

US 2012/0010322 A1   Jan. 12, 2012

(30) Foreign Application Priority Data

Jul. 8, 2010 (EP) ..................... 10168968

(51) Int. Cl.
*A61K 6/08* (2006.01)
*A61K 6/083* (2006.01)
*C07D 339/00* (2006.01)
*A61K 6/00* (2006.01)

(52) U.S. Cl.
CPC ............ *C07D 339/00* (2013.01); *A61K 6/0023* (2013.01); *A61K 6/083* (2013.01)
USPC ............ 523/116; 523/113; 523/115; 523/118; 433/228.1; 106/35; 549/11

(58) Field of Classification Search
CPC ......... A61K 6/08; A61K 6/083; C07D 339/00
USPC ............... 523/116, 113, 115, 118; 433/228.1; 106/35; 549/11
See application file for complete search history.

(56) References Cited

U.S. PATENT DOCUMENTS

| 6,043,361 | A | 3/2000 | Evans et al. | |
|---|---|---|---|---|
| 6,344,556 | B1 | 2/2002 | Evans et al. | |
| 6,479,592 | B2 | 11/2002 | Rheinberger et al. | |
| 7,365,222 | B2 | 4/2008 | Moszner et al. | |
| 7,501,457 | B2 * | 3/2009 | Angermann et al. | 523/116 |
| 7,585,901 | B2 | 9/2009 | Moszner et al. | |
| 2003/0008992 | A1 | 1/2003 | Dershem et al. | |
| 2005/0267254 | A1 | 12/2005 | Mizori et al. | |
| 2006/0223937 | A1 | 10/2006 | Herr et al. | |
| 2008/0076847 | A1 | 3/2008 | Moszner et al. | |
| 2008/0257493 | A1 * | 10/2008 | Dershem | 156/330 |
| 2008/0318188 | A1 * | 12/2008 | Stansbury et al. | 433/215 |
| 2009/0239967 | A1 | 9/2009 | Moszner et al. | |
| 2010/0113643 | A1 | 5/2010 | Dershem et al. | |

FOREIGN PATENT DOCUMENTS

| DE | 19616183 | 9/1997 |
|---|---|---|
| EP | 1413569 | 10/2003 |
| EP | 1905413 | 4/2008 |
| EP | 2103297 | 9/2009 |
| JP | 8300523 A | 11/1996 |
| JP | 11263884 A | 9/1999 |

OTHER PUBLICATIONS

Moszner et al., New developments of polymeric dental composites, Progress in Polymer Science, 2001, 26, pp. 535-576.
Moszner et al., Recent developments of new components for dental adhesives and composites, Macromolecular Materials and Engineering, 2007, 292, pp. 245-271.
Moszner et al., Synthesis and radical polymerization of bi- and trifunctional 2-vinylcyclopropanes, Polymerization of cyclic monomers, Macromol. Rapid Commun. 1997, 18, pp. 775-780.
Sadhir et al., Expanding Monomers, CRC Press, 1992.
Ullmann's Encyclopedia of Industrial Chemistry, 1987, A8, 5th Edition, VCH, Weinheim and New York, pp. 535-536.
Trujillo-Lemon al., Dimethacrylate derivatives of dimer acid, Journal of Polymer Science, 2006, 44, pp. 3921-3929.
De Meijere et al., Synthesis and radical polymerization of various 2-Cyclopropylacrylates, Eur. j. Org. Chem. 2004, VCH Verlag, pp. 3669-3678.
Evans et al., Free radical ring-opening polymerization of cyclic allylic sulfides: Liquid monomers with low polymerization volume shrinkage, Journal of Polymer Science, 2001, 39, pp. 202-215.

(Continued)

*Primary Examiner* — Michael Pepitone
(74) *Attorney, Agent, or Firm* — Ann M. Knab; Thad McMurray

(57) ABSTRACT

The invention relates to a radically polymerizable monomer of formula (I)

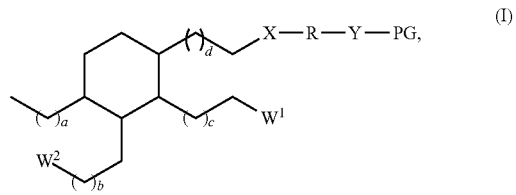

wherein
$W^1$ and $W^2$ in each case independently represent H or X—R—Y—PG, wherein at least one of $W^1$ and $W^2$ represents X—R—Y—PG,
X in each case independently is missing or represents an ether, ester, amide, urethane or urea group,
Y in each case independently is missing or represents an ether, ester, amide, urethane or urea group,
R in each case independently is missing or represents a $C_1$-$C_{16}$ alkylene radical which can be interrupted by one or more O atoms, wherein R can be missing only if X and/or Y is simultaneously also missing, and
PG in each case independently represents a cyclic, ring-opening polymerizable group,
a, b, c and d independently of each other can take the values 3 to 10.
The invention also relates to polymerizable compositions which comprise the monomers according to the invention, as well as their use as dental materials and for the preparation of dental materials, in particular composites, cements, adhesives or coatings.

23 Claims, No Drawings

(56) References Cited

OTHER PUBLICATIONS

Evans et al., Free-radical ring-opening polymerization of cyclic allylic sulfides. 2. Effect of substituents on seven- and eight-membered ring low shrink monomers, Macromolecules, 2000, 33, pp. 6722-6731.
Encyclopedia of Polymer Science and Engineering, 1988, 13, p. 754.
Fouassier et al., Radiation curing in polymer science and technology, 1993, II, Elsevier Applied Science, London and New York.
Jonsson S et al: "Recent advances in photoinduced donor/acceptor copolymerization", Nuclear Instruments & Methods in Physics Research, Section—B:Beam Interactions With Materials and Atoms, Elsevier, Amsterdam, NL LNKD- DOI:10.1016/S0168-583X(99)00110-X, vol. 151, No. 1-4, May 2, 1999, pp. 268-278.
Jönsson et al.: "Mechanistic aspects of donor structure in maleimide/donor photo-coplymerizations", Polymer Preprints, vol. 42, 2001, pp. 703-704, XP8128566.

* cited by examiner

DENTAL MATERIALS BASED ON DIMER ACID DERIVATIVES WITH RING OPENING POLYMERIZABLE GROUPS

CROSS-REFERENCE TO RELATED APPLICATIONS

This application claims the benefit of European Patent Application Serial No. 10168968.5, filed Jul. 8, 2010, which is hereby incorporated by reference in its entirety.

TECHNICAL FIELD

The present invention relates to monomers derived from hydrogenated dimer acids with ring-opening polymerizable groups, which are characterized by low polymerization shrinkage and which are suitable in particular for dental materials. The invention also relates to polymerizable compositions which comprise the monomers according to the invention, as well as their use as dental materials and for the preparation of dental materials, in particular composites, cements, adhesives or coatings.

BACKGROUND OF THE INVENTION

The polymerization of monomers such as vinyl compounds or (meth)acrylates usually involves a considerable volume contraction, which is also referred to as polymerization shrinkage. This polymerization shrinkage of the monomers used can lead for instance in the case of dental materials inter alia to disadvantageous shrinkage stresses and to the formation of marginal gaps in the case of filling composites, to reduced substrate adhesion in the case of fixing composites or coating materials as well as to the impairment of the dimensional stability of prosthesis plastics. Accordingly, low-shrinkage monomers have attracted much interest in the dental field (cf. N. Moszner, U. Salz, Progress Polymer Sci. 26 (2001) 535-576 and N. Moszner, U. Salz, Macromol. Mater. Eng. 292 (2007) 245-271).

Relatively low-shrinkage monomers used in the dental field are in particular the higher molecular weight dimethacrylate cross-linkers Bis-GMA and UDMA, which exhibit a polymerization shrinkage $\Delta V_p$ of 6.0 and 6.1 vol.-%, respectively. However, these cross-linkers have a very high viscosity (Bis-GMA: $\eta$=800-1000 Pa·s; UDMA: $\eta$=10 Pa·s), so that they usually have to be used in mixture with low-viscosity dimethacrylate diluents such as triethylene glycol dimethacrylate, which however exhibit a considerably higher polymerization shrinkage (triethylene glycol dimethacrylate: $\Delta V_p$=14.5 vol.-%).

Radically polymerizable cyclic monomers are generally characterized by a lower polymerization shrinkage as compared to linear monomers (cf. R. K. Sadhir, R. M. Luck, Expanding Monomers, CRC Press, Boca Raton etc. 1992). However, these monomers often have a considerably reduced reactivity as compared to linear monomers, whereby their practical applicability particularly in the dental field is limited considerably.

The term dimer acids generally refers to cyclic, particularly polyvalent, carboxylic acids which can be obtained by cyclodimerization of unsaturated fatty acids. Typically, these are cyclic di- or tricarboxylic acids that are obtainable for instance by alumina-catalyzed dimerization of unsaturated fatty acids, such as oleic acid, linoleic acid or tall oil. Such dimer acids usually have 36 carbon atoms on average (cf. Ullmann's Encyclopedia of Industrial Chemistry, 5th Ed., Vol. A8, VCH, Weinheim and New York 1987, pp. 535-536).

High-purity products are commercially available, which can contain for example the following unsaturated dimer acids:

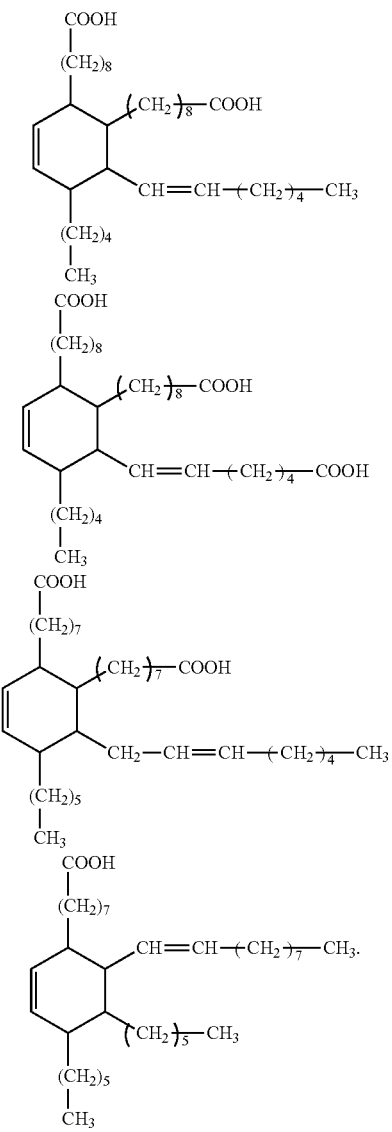

By hydrogenation of unsaturated dimer acids, the corresponding hydrogenated dimer acids are obtainable. For example, the following hydrogenated dimer acids can be obtained by hydrogenation of the unsaturated dimer acids shown above:

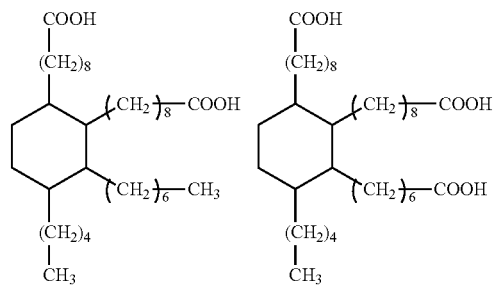

-continued

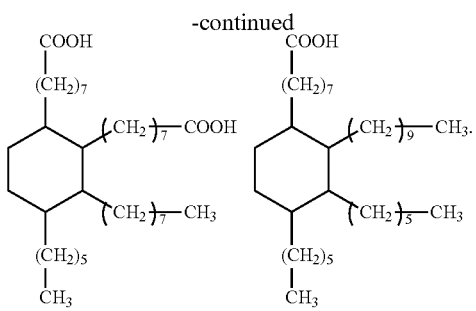

US 2008/0318188 A, which is hereby incorporated by reference, describes dimethacrylates derived from dimer acids and their use in dental compositions. These exhibit low shrinkage during polymerization, but produce polymer networks with high flexibility and low elastic modulus, which is disadvantageous in particular for use in dental materials such as filling composites (cf. M. Trujillo-Lemon, J. Ge, H. Lu, J. Tanaka, J. W. Stansbury, J. Polym. Sci., Part A: Polym. Chem. 44 (2006) 3921-3929).

SUMMARY OF THE INVENTION

It is therefore an object of the invention to provide monomers and dental materials based thereon which exhibit considerably lower polymerization shrinkage while having mechanical properties and reactivity, particularly with regard to radical photopolymerization, that are comparable to the materials conventionally based on methacrylates.

DETAILED DESCRIPTION OF THE INVENTION

This object is achieved in accordance with the invention by a radically polymerizable monomer of formula (I)

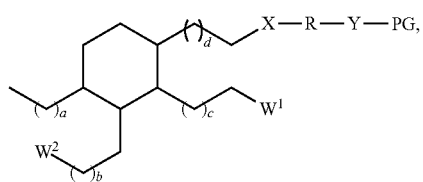

wherein
$W^1$ and $W^2$ in each case independently represent H or X—R—Y—PG, wherein at least one of $W^1$ and $W^2$ represents X—R—Y—PG,
X in each case independently is missing or represents an ether, ester, amide, urethane or urea group,
Y in each case independently is missing or represents an ether, ester, amide, urethane or urea group,
R in each case independently is missing or represents a $C_1$-$C_{16}$ alkylene radical which can be interrupted by one or more O atoms, wherein R can be missing only if X and/or Y is simultaneously also missing,
PG in each case independently represents a cyclic, ring-opening polymerizable group, and
a, b, c and d independently of each other can take the values 3 to 10.
Formula (I) and the other formulae shown herein cover all constitutionally isomeric and stereoisomeric forms as well as mixtures of various constitutionally isomeric and stereoisomeric forms such as e.g. racemates. The formulae cover only those compounds that are compatible with the chemical valence theory.

The indication that a radical can be interrupted for example by O atoms is to be understood to mean that these atoms or groups are inserted into the carbon chain of the radical, i.e. are bordered on both sides by carbon atoms. The number of these heteroatoms or groups is therefore at least 1 less than the number of carbon atoms, and the heteroatoms or groups cannot be terminal. According to the invention, radicals without heteroatoms are preferred in all cases where radicals can contain heteroatoms.

Preferred monomers of formula (I) are those wherein, independently of each other,
$W^1$ represents X—R—Y—PG,
$W^2$ represents H,
X in each case independently is missing or represents an ether, ester, amide or urethane group,
Y in each case independently is missing or represents an ether, ester, amide or urethane group,
R in each case independently is missing or represents a $C_1$-$C_{12}$ alkylene radical, in particular a $C_1$-$C_6$ alkylene radical and preferably a $C_1$-$C_3$ alkylene radical, which can be interrupted by one or more O atoms, wherein R can be missing only if X and/or Y is simultaneously also missing, and
a, b, c and d independently of each other can take the values 4 to 9, in particular 4 to 8, preferably 4 to 7 and in particular the values 4, 5, 6 and 7.

Particularly preferred are those monomers of formula (I) wherein
$W^1$ represents X—R—Y—PG,
$W^2$ represents H,
X in each case independently is missing or represents an ether, ester, amide or urethane group,
Y in each case independently is missing or represents an ether, ester, amide or urethane group,
R in each case independently is missing or represents a $C_1$-$C_{12}$ alkylene radical which can be interrupted by one or more O atoms, wherein R can be missing only if X and/or Y is simultaneously also missing, and
a, b, c and d independently of each other can take the values 4, 5, 6 and 7.

In one embodiment, the monomers of formula (I) are those of formula (Ia)

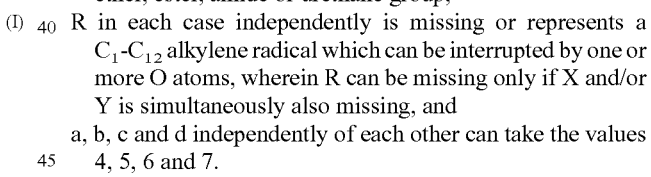

wherein
$W^{1'}$ and $W^{2'}$ in each case independently represent $CH_3$ or X'—R'—Y'—PG, wherein at least one of $W^{1'}$ and $W^{2'}$ represents X'—R'—Y'—PG,
X' in each case independently is missing or represents —$CH_2$—O—, —C(O)—O—, —$CH_2$—O—C(O)—, —C(O)—NH—, —$CH_2$—NH—C(O)—, —$CH_2$—NH—C(O)—O—, —$CH_2$—O—C(O)—NH— or —$CH_2$—NH—C(O)—NH—, Y' in each case independently is missing or represents —O—, —C(O)—O—, —O—C(O)—, —C(O)—NH—, —NH—C(O)—, —NH—C(O)—O—, —O—C(O)—NH— or —NH—C(O)—NH—, R' in each case independently is missing or represents a $C_1$-$C_{16}$ alkylene radical, in particular a $C_1$-$C_{12}$ alkylene radical, preferably a $C_1$-$C_6$ alkylene radical and most preferably a $C_1$-$C_3$ alkylene radical which can be interrupted by one or more O atoms, wherein R' can be missing only if X' and/or Y' is simultaneously also missing, PG in each case independently represents a cyclic, ring-opening polymerizable group, and a', b', c' and d' independently of each other can take the values 3 to 10, in particular 4 to 9, preferably 4 to 8, more preferably 4 to 7 and in particular the values 4, 5, 6 and 7.

It is preferred that $W^{1'}$ represents X'—R'—Y'—PG and $W^{2'}$ represents $CH_3$.

Preferred monomers of formula (Ia) are those wherein at least one and preferably all of the following variables have the indicated values:

a' is 3 to 10 and preferably 4 or 5,
b' is 3 to 10, in particular 3 to 9, preferably 3 to 6 and most preferably 4, 5 or 6,
c' is 3 to 10, in particular 3 to 9, preferably 6 to 9 and most preferably 6, 7 or 8,
d' is 3 to 10 and preferably 6 or 7.

It is particularly preferred that the sum of a' and d' is 11 and/or that the sum of b' and c' is 12.

Preferred ring-opening polymerizable groups PG are groups that are derived from cyclic allyl sulphide groups or vinylcyclopropane groups.

Particularly preferred ring-opening polymerizable groups PG are:

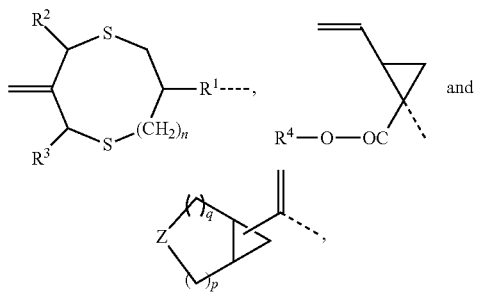

wherein
Z is selected from O, S,

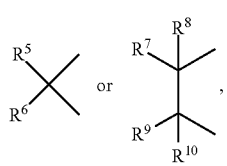

$R^1$ is missing or represents a $C_1$-$C_{16}$ alkylene radical which can be interrupted by one or more O atoms,
$R^2$ represents H or a $C_1$-$C_{10}$ alkyl radical,
$R^3$ represents H or a $C_1$-$C_{10}$ alkyl radical,
$R^4$ represents H or a $C_1$-$C_{10}$ alkyl radical,
$R^5$ represents H, —CO—$OR^{11}$, —CO—$R^{11}$ or $R^{11}$,
$R^6$ represents H, —CO—$OR^{11}$, —CO—$R^{11}$ or $R^{11}$,
$R^7$ to $R^{10}$ in each case independently represent H, —CO—$OR^{11}$, —CO—$R^{11}$, a $C_1$-$C_{15}$ alkyl radical which can be interrupted by one or more O atoms, a cycloaliphatic $C_4$-$C_{12}$ radical, a bicyclic $C_1$-$C_{12}$ radical, a $C_6$-$C_{14}$ aryl radical or a $C_7$-$C_{20}$ arylalkyl radical,
$R^{11}$ represents a $C_1$-$C_{15}$ alkyl radical which can be interrupted by one or more O atoms, a cycloaliphatic $C_4$-$C_{12}$ radical, a bicyclic $C_5$-$C_{12}$ radical, a $C_6$-$C_{14}$ aryl radical or a $C_7$-$C_{20}$ arylalkyl radical,
n is 0 or 1,
p is 0, 1, 2 or 3, and
q is 0, 1, 2 or 3.

Quite particularly preferred ring-opening polymerizable groups PG are:

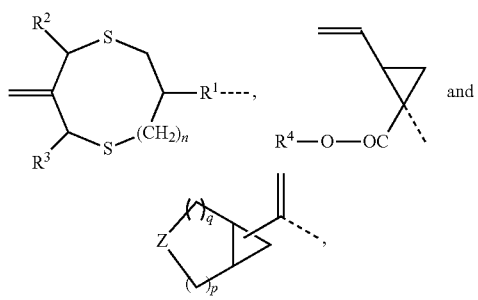

wherein
Z is selected from O, S,

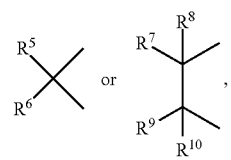

$R^1$ is missing or represents a $C_1$-$C_{10}$ alkylene radical which can be interrupted by one or more O atoms,
$R^2$ represents H or a $C_1$-$C_5$ alkyl radical,
$R^3$ represents H or a $C_1$-$C_5$ alkyl radical,
$R^4$ represents H or a $C_1$-$C_5$ alkyl radical,
$R^5$ represents H, —CO—$OR^{11}$, —CO—$R^{11}$ or $R^{11}$,
$R^6$ represents H, —CO—$OR^{11}$, —CO—$R^{11}$ or $R^{11}$,
$R^7$ to $R^{10}$ in each case independently represent H, —CO—$OR^{11}$, —CO—$R^{11}$, a $C_1$-$C_{15}$ alkyl radical which can be interrupted by one or more O atoms, a cycloaliphatic $C_4$-$C_6$ radical, a bicyclic $C_5$-$C_{12}$ radical, a phenyl radical or a benzyl radical,
$R^{11}$ represents a $C_1$-$C_{10}$ alkyl radical which can be interrupted by one or more O atoms, a cycloaliphatic $C_4$-$C_6$ radical, a phenyl radical or a benzyl radical,
n is 0 or 1,
P is 0, 1 or 2, and
q is 0, 1 or 2.

It was shown that the monomers according to the invention are characterized by an extremely low polymerization shrinkage and are therefore particularly suitable for the preparation of low-shrinkage dental materials. It was surprisingly shown that dental materials based on the monomers according to the invention have excellent mechanical properties and high reactivity, in particular with regard to radical photopolymerization, which are comparable to conventional dental materials based on methacrylates.

The monomers according to the invention of formula (I) can be obtained starting from suitably functionalized cyclic monomers by reaction with a hydrogenated dimer acid or a suitably functionalized derivative thereof.

Thus, monomers wherein X represents an ester group can be obtained by reaction of a hydrogenated dimer acid with a cyclic monomer of the formula HO—R—Y—PG:

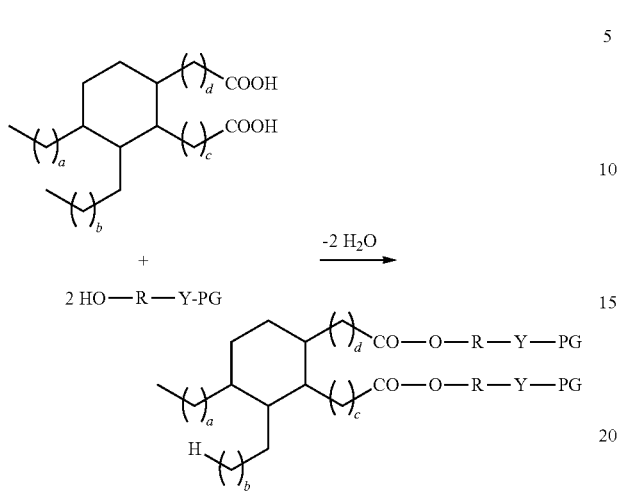

Specific Example

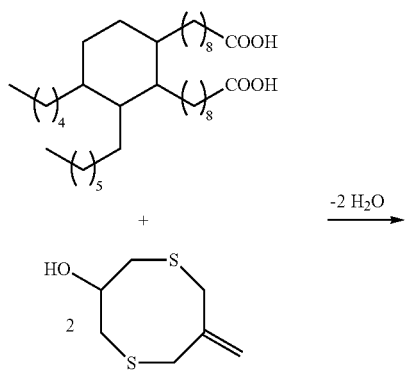

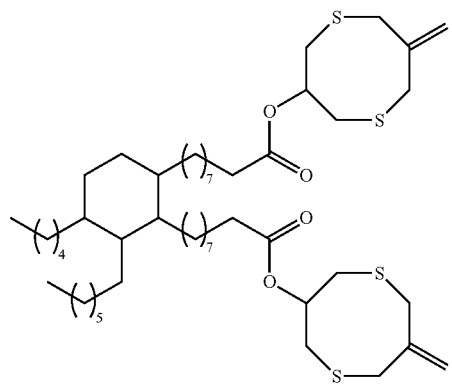

In other cases, it may be necessary to convert one or more carboxylic acid groups of the hydrogenated dimer acid into a suitable different functional group. Appropriate methods are known in principle from organic chemistry. Suitable methods for converting the carboxylic acid groups of hydrogenated dimer acids into different functional groups are also discussed for example in US 2008/0318188 A.

Suitably functionalized cyclic monomers for the synthesis of the monomers according to the invention of formula (I) are known from literature. For example, the synthesis of vinyl-cyclopropanes and of bicyclic cyclopropyl acrylates is described by N. Moszner et al. in Macromol. Rapid. Commun. 18 (1997) 775-780 and by A. de Meijere et al. in Eur. J. Org. Chem. (2004) 3669-3678, respectively, while the synthesis of functionalized cyclic allyl sulphides was described e.g. by R. A. Evans and E. Rizzardo in J. Polym. Sci., Part A. Polym. Chem. 39 (2001) 202-215 and Macromolecules 33 (2000) 6722-6731.

Some examples of the monomers according to the invention of formula (I) are listed below:

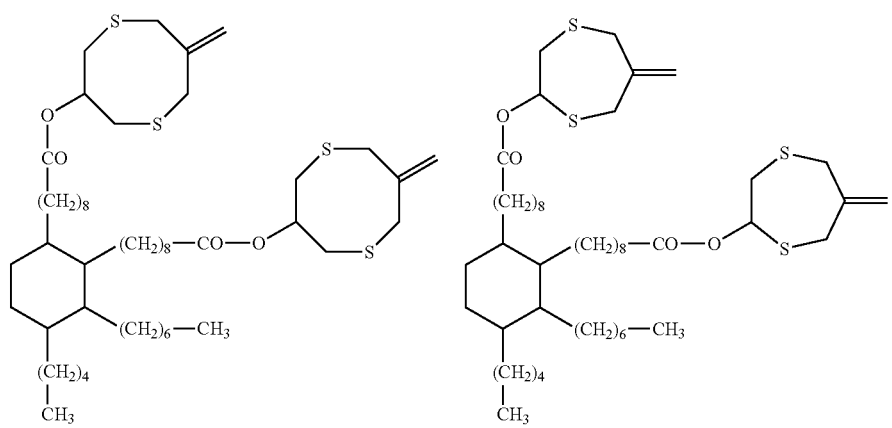

-continued
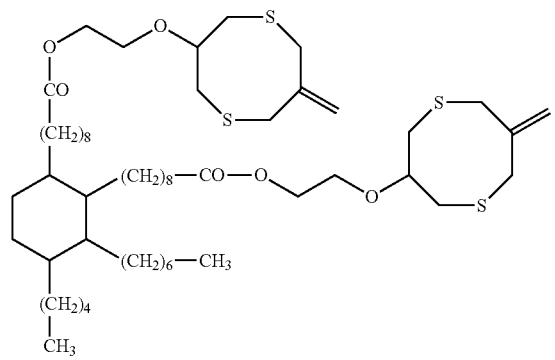
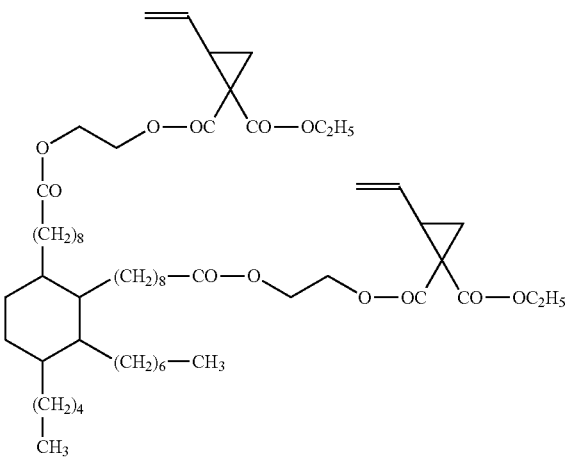
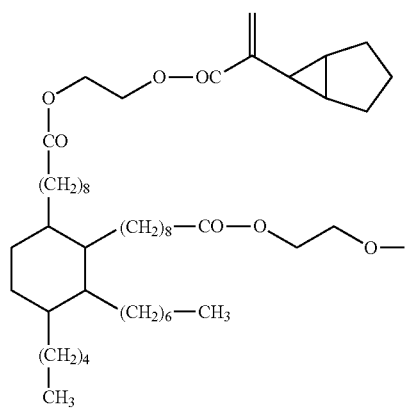
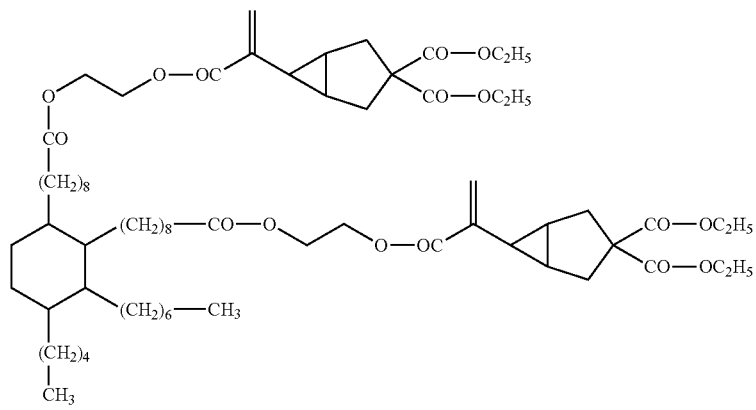
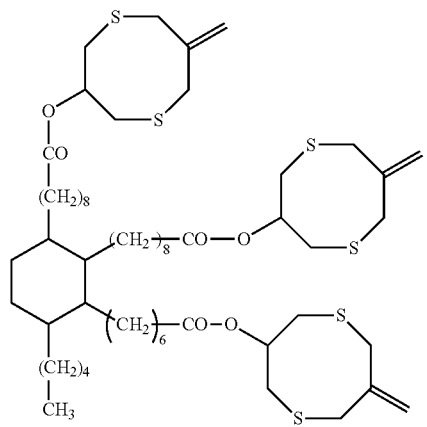
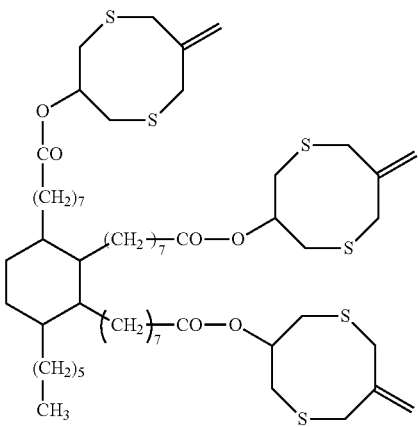

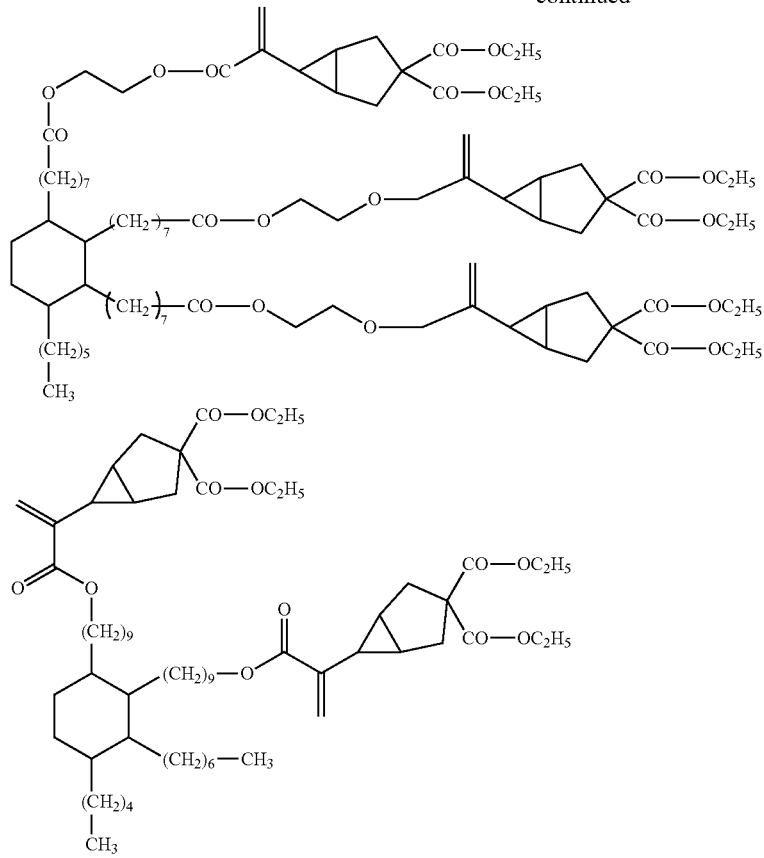

The invention also relates to a polymerizable composition which comprises at least one monomer of the above formula (I).

The compositions according to the invention based on the monomers of formula (I) can be polymerized with the known radical initiators, such as for example those described in Encyclopedia of Polymer Science and Engineering, Vol. 13, Wiley-Intersci. Pub., New York etc. 1988, 754 et seq. Photoinitiators, such as those known from J. P. Fouassier, J. F. Rabek (ed.), Radiation Curing in Polymer Science and Technology, Vol. II, Elsevier Applied Science, London and New York 1993 are particularly suitable. Benzoin ethers, dialkyl benzil ketals, dialkoxyacetophenones, acyl or bisacyl phosphine oxides, α-diketones such as 9,10-phenanthrenequinone, diacetyl, furil, anisil, 4,4'-dichlorobenzil and 4,4'-dialkoxybenzil and camphorquinone are preferred as photoinitiators for the UV or visible range. Norrish type I photoinitiators are also particularly suitable, especially acyl and bisacyl phosphine oxides as well as monoacyltrialkyl and diacyldialkyl germanium compounds, such as benzoyltrimethylgermanium, dibenzoyldiethylgermanium or bis(4-methoxybenzoyl)diethylgermanium. Suitable germanium initiators are described for example in EP 1 905 413 and EP 2 103 297. Mixtures of the different photoinitiators can also be used, such as e.g. dibenzoyldiethylgermanium in combination with camphorquinone and 4-dimethylaminobenzoic acid ethyl ester.

Furthermore, azo compounds, such as 2,2'-azobis(isobutyronitrile) (AIBN) or azobis(4-cyanovaleric acid), or peroxides, such as dibenzoyl peroxide, dilauroyl peroxide, tert-butyl peroctoate, tert-butyl perbenzoate or di-(tert-butyl) peroxide, can also be used as initiators for the radical polymerization. Benzopinacol and 2,2'-dialkylbenzopinacols are particularly suitable as initiators for hot-curing.

Peroxides and α-diketones are used preferably in combination with aromatic amines to accelerate the initiation. Preferred redox systems are combinations of benzoyl peroxide or camphorquinone with amines, such as N,N-dimethyl-p-toluidine, N,N-dihydroxyethyl-p-toluidine, p-dimethylaminobenzoic acid ethyl ester or structurally related systems. In addition, redox systems comprising peroxides in combination with ascorbic acid, barbiturates or sulphinic acids are also suitable.

The compositions according to the invention can comprise one or more monomers of formula (I). In addition to the monomers of formula (I), they can also comprise further radically polymerizable monomers with one or more radically polymerizable groups. Dental materials which comprise at least one further radically polymerizable monomer with 2 or more, preferably 2 to 3 radically polymerizable groups, are particularly preferred. Polyfunctional monomers have cross-linking properties.

Preferred additional monomers are mono- or polyfunctional (meth)acrylates or (meth)acrylamides ((meth)acrylic compounds). By monofunctional (meth)acrylic compounds are meant compounds with one, by polyfunctional (meth)acrylic compounds are meant compounds with two or more, preferably 2 to 3 (meth)acrylic groups.

Preferred polyfunctional monomers are bisphenol-A-di(meth)acrylate, bis-GMA (an addition product of methacrylic acid and bisphenol-A-diglycidyl ether), ethoxylated bisphenol-A-di(meth)acrylate, UDMA (an addition product of 2-hydroxyethyl methacrylate and 2,2,4-trimethyl hexamethylene diisocyanate), di-, tri- or tetraethylene glycol di(meth)acrylate, trimethylolpropane tri(meth)acrylate, pentaerythritol tetra(meth)acrylate as well as butanediol di(meth)acrylate, 1,10-decanediol di(meth)acrylate or 1,12-dodecanediol di(meth)acrylate.

Quite particularly preferred are mixtures of monomers of formula (I) mixed with known low-shrinkage radically ring-opening polymerizable monomers, such as mono- or multifunctional vinylcyclopropanes or bicyclic cyclopropane derivatives, preferably the monomers disclosed in DE 196 16 183 C2 and U.S. Pat. No. 6,479,592, which is hereby incorporated by reference, and EP 1 413 569 A1, U.S. Pat. No. 7,365,222 and U.S. Pat. No. 7,585,901, which are hereby incorporated by reference, or cyclic allyl sulphides, preferably the monomers disclosed in U.S. Pat. No. 6,043,361 and U.S. Pat. No. 6,344,556, which are hereby incorporated by reference. Moreover, mixtures of monomers of formula (I) with at least one further ring-opening polymerizable monomer and at least one radically polymerizable monomer with two or more radically polymerizable groups, in particular the polyfunctional (meth)acrylate compounds listed above, are further preferred.

Particularly preferred ring-opening polymerizable monomers are vinylcyclopropanes, such as 1,1-di(ethoxycarbonyl)- or 1,1-di(methoxycarbonyl)-2-vinylcyclopropane or the esters of 1-ethoxycarbonyl- or 1-methoxycarbonyl-2-vinylcyclopropane carboxylic acid with ethylene glycol, 1,1,1-trimethylolpropane, 1,4-cyclohexanediol or resorcinol. Preferred bicyclic cyclopropane derivatives are 2-(bicyclo[3.1.0]hex-1-yl)acrylic acid methyl or ethyl ester or their disubstitution products in the 3-position such as (3,3-bis-(ethoxycarbonyl)bicyclo[3.1.0]hex-1-yl)acrylic acid methyl or ethyl ester. Preferred cyclic allyl sulphides are in particular the addition products of 2-(hydroxymethyl)-6-methylene-1,4-dithiepan or 7-hydroxy-3-methylene-1,5-dithiacyclooctane with 2,2,4-trimethylhexymethylene-1,6-diisocyanate or an asymmetric hexamethylene diisocyanate trimer such as Desmodur XP 2410 from Bayer AG.

Furthermore, the compositions according to the invention based on the monomers of formula (I) can comprise one or more fillers, preferably organic or inorganic particulate fillers. Fillers with an average particle diameter of 10 nm to 5 μm are particularly suitable. Preferred inorganic particulate fillers are amorphous spherical nanoparticulate fillers based on oxides, such as pyrogenic silicic acid or precipitation silicic acid, $ZrO_2$ and $TiO_2$, or mixed oxides of $SiO_2$, $ZrO_2$ and/or $TiO_2$, preferably with an average particle diameter of 10 to 200 nm, microfine fillers, mini fillers, such as quartz powder, glass ceramic powder or glass powder with an average particle size of 0.2 to 5 μm as well as x-ray opaque fillers, such as ytterbium trifluoride or nanoparticulate tantalum (V) oxide or barium sulphate. In addition, fibrous fillers such as glass fibres, polyamide fibres or carbon fibres can also be used.

Finally, further additives, such as e.g. stabilizers, UV-absorbers, colorants or pigments as well as solvents or lubricants, can be added to the compositions according to the invention based on the monomers of formula (I) where necessary.

Compositions which comprise the following components are preferred according to the invention:
(a) 1 to 90 wt.-%, preferably 1 to 80 wt.-% and particularly preferably 5 to 70 wt.-% monomer of formula (I),
(b) 0.01 to 10 wt.-%, particularly preferably 0.1 to 3.0 wt.-% initiator for the radical polymerization,
(c) 0 to 80 wt.-%, preferably 0 to 60 wt.-% and particularly preferably 5 to 50 wt.-% further radically polymerizable monomers, preferably 5 to 80 wt.-% further ring-opening polymerizable monomer and 0 to 50 wt.-% polyfunctional (meth)acrylate,
(d) 0 to 85 wt.-% filler,
(e) optionally 0.01 to 50 wt.-%, preferably 0.05 to 5 wt.-% and particularly preferably 0.1 to 2 wt.-% additive, and
(f) 0 to 95 wt.-%, preferably 0 to 70 wt.-% and particularly preferably 0 to 50 wt.-% solvent.

All percentages relate to the total mass of the composition unless otherwise stated.

The compositions according to the invention are particularly suitable as dental materials, in particular as composite, cement, adhesive or coating material.

The preferred composition of the materials for dental applications is based on the desired application.

Preferred adhesives and coating materials comprise the following components:
(a) 1 to 90 wt.-%, preferably 1 to 80 wt.-% and particularly preferably 5 to 70 wt.-% monomer of formula (I),
(b) 0.01 to 10 wt.-%, particularly preferably 0.1 to 2.0 wt.-% initiator for the radical polymerization,
(c) 0 to 80 wt.-%, preferably 0 to 60 wt.-% and particularly preferably 5 to 50 wt.-% further radically polymerizable monomers, preferably 5 to 80 wt.-% further ring-opening polymerizable monomer and 0 to 50 wt.-% polyfunctional (meth)acrylate,
(d) 0 to 85 wt.-% and preferably 0 to 20 wt.-% filler,
(e) optionally 0.01 to 50 wt.-%, preferably 0.05 to 5 wt.-% and particularly preferably 0.1 to 2 wt.-% additive, and
(f) 0 to 95 wt.-%, preferably 0 to 70 wt.-% and particularly preferably 0 to 50 wt.-% solvent.

Preferred cements comprise the following components:
(a) 1 to 90 wt.-%, preferably 1 to 70 wt.-% and particularly preferably 5 to 30 wt.-% monomer of formula (I),
(b) 0.01 to 10 wt.-%, particularly preferably 0.1 to 2.0 wt.-% initiator for the radical polymerization,
(c) 0 to 80 wt.-%, preferably 0 to 50 wt.-% and particularly preferably 5 to 30 wt.-% further radically polymerizable monomers, preferably 5 to 30 wt.-% further ring-opening polymerizable monomer and 0 to 10 wt.-% polyfunctional (meth)acrylate,
(d) 0 to 85 wt.-% and particularly preferably 20 to 70 wt.-% filler, and
(e) optionally, 0.01 to 50 wt.-%, preferably 0.05 to 5 wt.-% and particularly preferably 0.1 to 5 wt.-% additive.

Preferred composites comprise the following components:
(a) 1 to 90 wt.-%, preferably 1 to 70 wt.-% and particularly preferably 5 to 20 wt.-% monomer of formula (I),
(b) 0.01 to 10 wt.-%, particularly preferably 0.1 to 2.0 wt.-% initiator for the radical polymerization,
(c) 0 to 80 wt.-%, preferably 0 to 50 wt.-% and particularly preferably 5 to 20 wt.-% further radically polymerizable monomers, preferably 5 to 20 wt.-% further ring-opening polymerizable monomer and 0 to 10 wt.-% polyfunctional (meth)acrylate,
(d) 0 to 85 wt.-% and particularly preferably 20 to 85 wt.-% filler, and
(e) optionally, 0.01 to 50 wt.-%, preferably 0.05 to 5 wt.-% and particularly preferably 0.1 to 2 wt.-% additive.

The present invention also relates to the use of radically polymerizable monomers of formula (I), or polymerizable compositions which comprise at least one monomer of formula (I), as dental material and in particular for the preparation of dental materials, preferably the dental materials described above.

The invention also relates to a process for the preparation of shaped bodies, such as crowns, bridges, inlays and artificial teeth, wherein a composition according to the invention is formed into the shaped body in a manner known per se and is then at least partially, preferably completely, cured. The curing is preferably effected by radical polymerization.

The invention is described in further detail below with reference to examples.

EXAMPLES

Example 1

Synthesis of a Ring-Opening Polymerizable Hydrogenated Dimer Acid Derivative RODA 21.09 g (0.110 mol) N-(3-dimethylaminopropyl)-N'-ethylcarbodiimide hydrochloride was added portionwise at 0° C. within 2 h to a solution of 17.63 g (0.100 mol) 7-methylene-1,5-dithiacyclooctan-3-ol, 28.25 g (0.050 mol) dimer acid and 0.611 g (0.005 mol) 4-dimethylaminopyridine in 200 ml anhydrous methylene chloride. After 6 h of stiffing at 0° C., 500 ml water was added to the reaction mixture. After phase separation, the organic phase was washed with 2 N hydrochloric acid (2×100 ml) and water (2×100 ml), dried with anhydrous sodium sulphate and the solvent was removed. After chromatographic purification over silica gel (hexane/ethyl acetate 4:1), 24.10 g (55%) of a colorless, viscous liquid ($\eta$=7.70 Pa·s) was obtained.

$^1$H-NMR (400 MHz, CDCl$_3$): δ (ppm)=0.83-0.90, 1.04-1.47, 1.57-1.60 (3 m, 62H, CH, CH$_2$, CH$_3$; a), 2.27 (t, J=7.5 Hz, 4H, O=C—CH$_2$; b), 3.02 and 3.03 (2 d, J=1.68 Hz, 3.28 Hz, in each case 8H, SCH$_2$—CHO; c), 3.24 (d, J=2.6 Hz, 8H, SCH$_2$—C=; d), 4.99-5.05 (m, 2H, OCH; e), 5.24 (s, 4H, =CH$_2$; f).

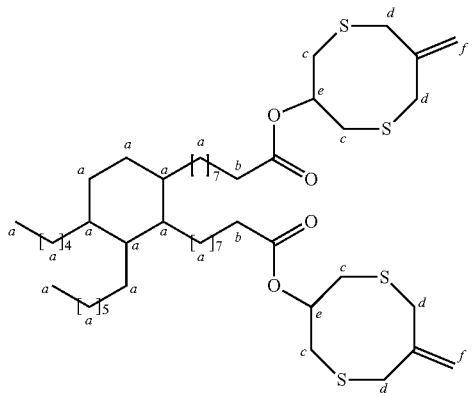

$^{13}$C-NMR (100 MHz, CDCl$_3$): δ (ppm)=14.1 (CH$_3$; a), 22.7-34.4 (CH, CH$_2$; b), 32.7, 37.9 (SCH$_2$; c), 72.3 (OCH; d), 120.4 (=CH$_2$; e), 145.0 (C=CH; f), 173.0 (C=O; g).

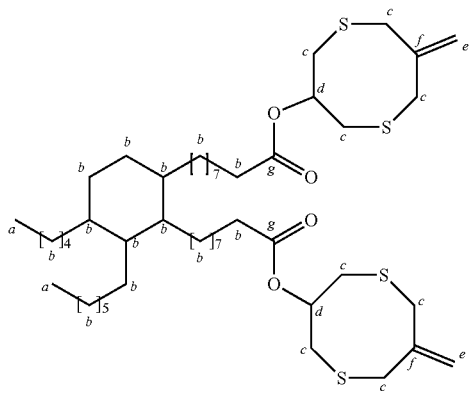

IR (diamond ATR): v=3060 (w, =CH), 2921, 2852 (s, CH$_2$, CH$_3$), 1734 (s, C=O), 1633 (w, C=C), 1457 (m, CH$_2$, CH$_3$), 1377 (m, CH$_3$), 1160, 1092 (s, CSC, COC), 903 cm$^{-1}$ (s, =CH).

Example 2

Synthesis of a Methacrylated Dimer Acid Derivative DMDA

Comparative Example 30.46 g (0.240 mol) oxalyl chloride was added dropwise at room temperature to a solution of 45.20 g (0.080 mol) dimer acid and 0.438 g (0.006 mol) N,N-dimethylformamide in 250 ml anhydrous toluene. After 2 h, the excess oxalyl chloride and the solvent were distilled off (60° C., 40 mbar). The brown residue obtained was taken up in 250 ml anhydrous methylene chloride and added dropwise at room temperature to a solution of 20.82 g (0.160 mol) 2-hydroxyethyl methacrylate and 17.0 g (0.168 mol) triethylamine in 250 ml anhydrous methylene chloride. After 1 h, the reaction mixture was washed with 1 N hydrochloric acid (2×100 ml), saturated sodium hydrogen carbonate solution (2×100 ml) and water (2×100 ml), the organic phase was dried with anhydrous sodium sulphate and the solvent was removed in vacuum. After chromatographic purification over silica gel (methylene chloride/ethyl acetate 4:1), 31.20 g (51%) of an orange, slightly viscous liquid ($\eta$=0.35 Pa·s) was obtained.

$^1$H-NMR (400 MHz, CDCl$_3$): δ (ppm)=0.83-0.90, 1.04-1.47, 1.60-1.64 (3 m, 62H, CH, CH$_2$, CH$_3$; a), 1.95 (s, 6H, CH$_3$; b), 2.32 (t, J=7.5 Hz, 4H, O=C—CH$_2$; c), 4.31-4.36 (m, 8H, OCH$_2$; d), 5.59, 6.13 (2 s, in each case 2H, =CH$_2$; e).

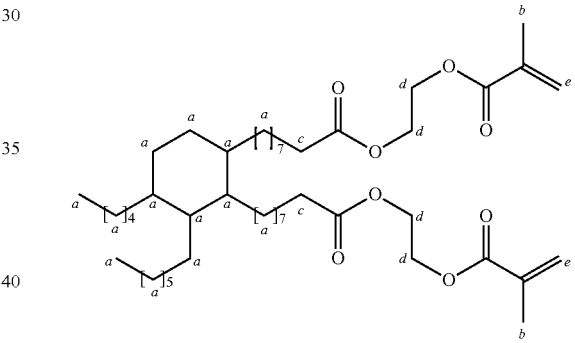

$^{13}$C-NMR (100 MHz, CDCl$_3$): δ (ppm)=14.1, 18.3 (CH$_3$; a), 22.7-34.2 (CH, CH$_2$; b), 61.9, 62.5 (OCH$_2$; c), 126.0 (=CH$_2$; d), 136.0 (C=CH$_2$; e), 167.1, 173.0 (C=O; f).

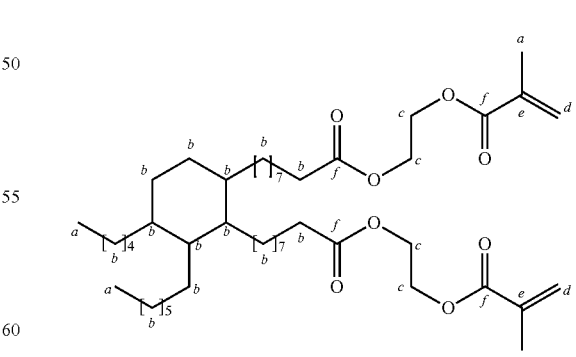

IR (diamond ATR): v=3090 (w, =CH), 2923, 2853 (s, CH$_2$, CH$_3$), 1735, 1722 (s, C=O), 1638 (w, C=C), 1455 (m, CH$_2$, CH$_3$), 1376 (m, CH$_3$), 1152 (vs, COC), 939 cm$^{-1}$ (m, =CH).

Example 3

Preparation of a Dental Composite Based on Polymerizable Dimer Acid Derivatives from Example 1 and Example 2

Composites based on a methacrylate mixture with the dimer acid dimethacrylate DMDA from Example 2 (Composite A, comparative) and including the ring-opening polymerizable dimer acid derivative RODA from Example 1 (Composite B) were prepared according to Table 1, given below, by means of a kneader (Linden). Corresponding testpieces were prepared from the materials, which were irradiated twice for 3 minutes with a dental light source (Spectramat®, Ivoclar Vivadent AG) and thereby cured. The bending strength, the bending E modulus and the polymerization shrinkage were determined according to ISO standard ISO 4049 (Dentistry—Polymer-based filling, restorative and luting materials).

TABLE 1

Composition of the composites (figures in mass-%)

| Substances | Composite A Proportions (wt.-%) | Composite B Proportions (wt.-%) |
| --- | --- | --- |
| Bis-GMA[1] | 6.92 | 6.92 |
| TEGDMA[2] | 4.85 | 4.85 |
| DMDA | 6.21 | — |
| RODA | — | 6.21 |
| Aerosil OX-50[3] | 1.00 | 1.00 |
| Glass filler GM 27884[4] | 51.61 | 51.61 |
| Spherosil[5] | 14.39 | 14.39 |
| Ytterbium trifluoride[6] | 14.89 | 14.89 |
| Photoinitiator[7] | 0.13 | 0.13 |

[1] Bis-GMA (Esschem)
[2] triethylene glycol dimethacrylate (Esschem)
[3] silanized pyrogenic SiO$_2$ (Degussa)
[4] silanized Ba—Al-borosilicate glass filler (Schott) with an average particle size of 1.5 μm
[5] SiO$_2$—ZrO$_2$ mixed oxide (Tokuyama Soda, average primary particle size: 250 nm)
[6] YbF$_3$ (Rhone-Poulenc) with an average particle size of 200 nm
[7] bis(4-methoxybenzoyl)diethylgermanium It can be seen from Table 2 that Composite B based on a ring-opening polymerizable dimer acid derivative according to the invention exhibits a considerably reduced polymerization shrinkage as compared to Composite A based on a dimer acid dimethacrylate while having comparable mechanical properties.

TABLE 2

Composite properties

| Property | Composite A | Composite B |
| --- | --- | --- |
| Bending strength (MPa) after 24 h | 129 | 140 |
| Bending strength (MPa) after 24 h WI[1] | 149 | 124 |
| Bending E modulus (GPa) after 24 h | 10.1 | 9.8 |
| Bending E modulus (GPa) after 24 h WI | 9.7 | 8.7 |
| Polymerization shrinkage (vol.-%) | 3.0 | 1.9 |

[1] WI = water immersion of the testpieces

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. A radically polymerizable monomer of formula (I)

wherein
W$^1$ and W$^2$ in each case independently represent H or X—R—Y—PG, wherein at least one of W$^1$ and W$^2$ represents X—R—Y—PG,
X in each case independently is missing or represents an ether, ester, amide, urethane or urea group,
Y in each case independently is missing or represents an ether, ester, amide, urethane or urea group,
R in each case independently is missing or represents a C$_1$-C$_{16}$ alkylene radical which can be interrupted by one or more O atoms, wherein R can be missing only if X and/or Y is simultaneously also missing,
PG in each case independently represents a cyclic, ring-opening polymerizable group, selected from wherein
Z is selected from O, S, R1 is missing or represents a C1-C16 alkylene radical which can be interrupted by one or more O atoms,
R2 represents H or a C1-C10 alkyl radical,
R3 represents H or a C1-C10 alkyl radical,
R4 represents H or a C1-C10 alkyl radical,
R5 represents H, —CO—OR11, —CO—R11 or R11,
R6 represents H, —CO—R11, —CO—R11 or R11,
R7 to R10 in each case independently represent H, —CO—R11, —CO—R11, a C1-C15 alkyl radical which can be interrupted by one or more O atoms, a cycloaliphatic C4-C12 radical, a bicyclic C5-C12 radical, a C6-C14 aryl radical or a C7-C20 arylalkyl radical, $R^{11}$ represents a C1-C15 alkyl radical which can be interrupted by one or more O atoms, a cycloaliphatic C4-C12 radical, a bicyclic C5-C12 radical, a C6-C14 aryl radical or a C7-C20 arylalkyl radical, n is 0 or 1, p is 0, 1, 2 or 3, q is 0, 1, 2 or 3 and a, b, c and d independently of each other can take the values 3 to 10.

2. The monomer according to claim 1, wherein the ring-opening polymerizable group PG is independently selected from:

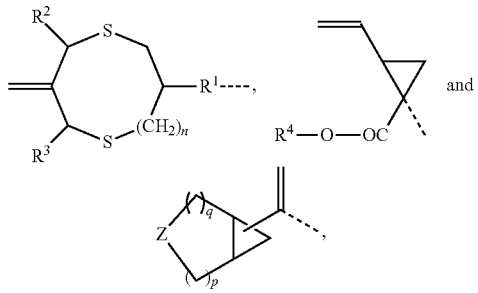

wherein

Z is selected from O, S,

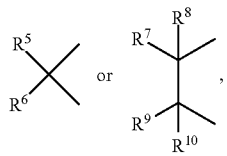

$R^1$ is missing or represents a $C_1$-$C_{10}$ alkylene radical which can be interrupted by one or more O atoms, $R^2$ represents H or a $C_1$-$C_5$ alkyl radical, $R^3$ represents H or a $C_1$-$C_5$ alkyl radical, $R^4$ represents H or a $C_1$-$C_5$ alkyl radical, $R^5$ represents H, —CO—$OR^{11}$, —CO—$R^{11}$ or $R^{11}$, $R^6$ represents H, —CO—$OR^{11}$, —CO—$R^{11}$ or $R^{11}$, $R^7$ to $R^{10}$ in each case independently represent H, —CO—$OR^{11}$, —CO—$R^{11}$, a $C_1$-$C_{15}$ alkyl radical which can be interrupted by one or more O atoms, a cycloaliphatic $C_4$-$C_6$ radical, a bicyclic $C_5$-$C_{12}$ radical, a phenyl radical or a benzyl radical, $R^{11}$ represents a $C_1$-$C_{10}$ alkyl radical which can be interrupted by one or more O atoms, a cycloaliphatic $C_4$-$C_6$ radical, a phenyl radical or a benzyl radical, n is 0 or 1, p is 0, 1 or 2 and q is 0, 1 or 2.

3. A polymerizable composition which comprises at least one monomer according to claim 1.

4. The composition according to claim 3 which further comprises an initiator for the radical polymerization.

5. The composition according to claim 3 which further comprises at least one further radically polymerizable monomer.

6. The composition according to claim 5 which comprises at least one monomer selected from bisphenol-A-di(meth)acrylate, Bis-GMA, ethoxylated bisphenol-A-di(meth)acrylate, UDMA, di-, tri- or tetraethylene glycol di(meth)acrylate, trimethylolpropane tri(meth)acrylate, pentaerythritol tetra(meth)acrylate, butanediol di(meth)acrylate, 1,10-decanediol di(meth)acrylate or 1,12-dodecanediol di(meth)acrylate.

7. The composition according to claim 5 which comprises at least one radically ring-opening polymerizable monomer selected from mono- and multifunctional vinylcyclopropanes, bicyclic cyclopropanes or cyclic allyl sulphides.

8. The composition according to claim 3 which further comprises at least one filler.

9. Composition according to claim 3 which further comprises at least one additive selected from stabilizers, UV-absorbers, colorants, pigments, solvents or lubricants.

10. The composition according to claim 3 which comprises
 (a) 1 to 90 wt.-% monomer of formula (I),
 (b) 0.01 to 10 wt.-% initiator for the radical polymerization,
 (c) 0 to 80 wt.-% further radically polymerizable monomers,
 (d) 0 to 85 wt.-% filler,
 (e) optionally 0.01 to 50 wt.-% additive, and
 (f) 0 to 95 wt.-% solvent.

11. A dental material comprising the radically polymerizable monomer according to claim 1.

12. The dental material according to claim 11, which is a composite, cement, adhesive or coating material.

13. A dental material comprising the polymerizable composition according to claim 3.

14. The dental material according to claim 13, which is a composite, cement, adhesive or coating material.

15. A method comprising using the radically polymerizable monomer according to claim 1 for the preparation of a dental material.

16. The method according to claim 15, wherein the dental material is a composite, cement, adhesive or coating material.

17. A method comprising using the polymerizable composition according to claim 3 for the preparation of a dental material.

18. The method according to claim 17, wherein the dental material is a composite, cement, adhesive or coating material.

19. A method for the preparation of a shaped body wherein a composition according to claim 3 is formed into a body with the desired shape and is then completely or partially cured.

20. The composition according to claim 5 wherein the at least one further radically polymerizable monomer comprises at least one further radically polymerizable monomer with two or more radically polymerizable groups.

21. The composition according to claim 10 which comprises
 (a) 1 to 80 wt.-% monomer of formula (I),
 (b) 0.1 to 3.0 wt.-% initiator for the radical polymerization,
 (c) 0 to 60 wt.-% further radically polymerizable monomers,
 (d) 0 to 85 wt.-% filler,
 (e) optionally 0.05 to 5 wt.-% additive, and
 (f) 0 to 70 wt.-% solvent.

22. The composition according to claim 10 which comprises
 (a) 5 to 70 wt.-% monomer of formula (I),
 (b) 0.1 to 3.0 wt.-% initiator for the radical polymerization,
 (c) 5 to 50 wt.-% further radically polymerizable monomers,
 (d) 0 to 85 wt.-% filler,
 (e) optionally 0.1 to 2 wt.-% additive, and
 (f) 0 to 50 wt.-% solvent.

23. The composition according to claim 10 wherein the further radically polymerizable monomers comprise 5 to 80 wt.-% further ring-opening polymerizable monomer and 0 to 50 wt.-% polyfunctional (meth)acrylate.

* * * * *